(12) United States Patent
Dunn et al.

(10) Patent No.: US 12,408,642 B2
(45) Date of Patent: Sep. 9, 2025

(54) OVIPOSITION TRAYS FOR INSECT EGGS

(71) Applicant: PreZero US, Inc., Los Angeles, CA (US)

(72) Inventors: Kieron James Dunn, Cape Town (CA); Cameron Spencer Richards, Singapore (SG); Jacobus Adriaan Kotze, Cape Town (CA)

(73) Assignee: PreZero US, Inc., Los Angeles, CA (US)

( * ) Notice: Subject to any disclaimer, the term of this patent is extended or adjusted under 35 U.S.C. 154(b) by 0 days.

(21) Appl. No.: 17/911,796

(22) PCT Filed: Mar. 16, 2020

(86) PCT No.: PCT/IB2020/052372
§ 371 (c)(1),
(2) Date: Sep. 15, 2022

(87) PCT Pub. No.: WO2021/186209
PCT Pub. Date: Sep. 23, 2021

(65) Prior Publication Data
US 2023/0137385 A1 May 4, 2023

(51) Int. Cl.
*A01K 67/30* (2025.01)
(52) U.S. Cl.
CPC .................. *A01K 67/30* (2025.01)
(58) Field of Classification Search
CPC ..... A01K 67/033; A01K 67/30; A01K 67/362
See application file for complete search history.

(56) References Cited

U.S. PATENT DOCUMENTS

| 5,351,643 A * | 10/1994 | Hughes | A01K 67/033 119/6.5 |
| 8,733,284 B2 * | 5/2014 | Courtright | A01K 67/033 119/6.6 |

(Continued)

FOREIGN PATENT DOCUMENTS

| WO | WO-2015013826 A1 * | 2/2015 | A01M 1/106 |
| WO | WO-2016153339 A1 * | 9/2016 | A01K 67/033 |

OTHER PUBLICATIONS

International Preliminary Report on Patentability; Application No. PCT/IP2020/052372 mailing date Sep. 20, 2022—7 pages.

(Continued)

*Primary Examiner* — Joshua J Michener
*Assistant Examiner* — Aaron M Rodziwicz
(74) *Attorney, Agent, or Firm* — K&L Gates LLP; Dennis A. Majewski

(57) ABSTRACT

An oviposition tray for ovipositioning of insect eggs, such as eggs of adult female black soldier flies, comprises a plastics oviposition tray body in the form of a planar block having a front and rear sides. The front side has a flat face defining a plurality of spaced, parallel, elongate egg laying recesses. Each recess has a length of between 8 mm and 25 mm, optimally approximately 17 mm, a width of between 1 mm and 6 mm, optimally approximately 2 mm, and a depth of not less than 2 mm. The oviposition tray body defines a number of ventilation apertures allowing for an airborne attractant to flow through the oviposition tray body for attracting insects to the oviposition try body to lay eggs. The oviposition tray body includes four spacers for spacing the oviposition tray body from other similar oviposition tray bodies in a stacked configuration of the oviposition tray bodies.

22 Claims, 7 Drawing Sheets

(56) References Cited

U.S. PATENT DOCUMENTS

| | | | | |
|---|---|---|---|---|
| 9,462,795 | B2* | 10/2016 | Chin | A01K 67/033 |
| 10,188,087 | B2* | 1/2019 | Leo | C11C 1/10 |
| D841,898 | S * | 2/2019 | Selby | A01K 67/033 |
| | | | | D30/120 |
| 10,362,772 | B2* | 7/2019 | Arsiwalla | A01K 67/033 |
| 10,448,623 | B1* | 10/2019 | Selby | A01K 67/033 |
| 11,395,474 | B2* | 7/2022 | Hall | A01K 67/033 |
| 2017/0042131 | A1* | 2/2017 | Unger | A01K 67/033 |
| 2019/0133096 | A1* | 5/2019 | Li | A01K 67/033 |
| 2020/0275643 | A1* | 9/2020 | Metlitz | A01K 1/0076 |

OTHER PUBLICATIONS

International Search Report and Written Opinion, mailed Oct. 14, 2020, for International Application Serial No. PCT/IB2020/052372 filed Mar. 16, 2020.

* cited by examiner

OVIPOSITION TRAYS FOR INSECT EGGS

PRIORITY CLAIM

The present application is a national phase filing of International Application No. PCT/IB2020/052372, filed on Mar. 16, 2020, the entire contents of which are incorporated herein by reference and relied upon.

FIELD OF THE INVENTION

This invention relates to oviposition trays for insects. It relates particularly to oviposition trays for ovipositioning of insect eggs of a variety of useful insect species such as, but not necessarily limited to, the black soldier fly (BSF).

BACKGROUND TO THE INVENTION

In a commercial BSF farming operation, a colony of mature BSF are typically held in a breeding cage where they breed and deposit eggs onto strategically positioned laying surfaces. Eggs are collected from the laying surfaces for hatching and emergent neonate larvae are apportioned into two streams wherein a lifecycle stream (typically about 5%) is returned to the fly colony to pupate and a production stream (typically about 95%) is collected for further commercial processing into various products.

In a commercial BSF farming operation, it is essential to provide adult female BSF with a desirable oviposition site in order to encourage oviposition. This should ideally take place in a localized area in order to aid egg collection.

When searching for an oviposition site, BSF females will naturally seek out oviposition sites that will provide some benefit to the eggs and emergent larvae. Such sites typically include recesses which act as a physical barrier and protection for eggs and emergent neonate larvae, a food source nearby and away from brightly lit areas that could result in dehydration of the eggs and of neonate larvae post-emergence.

In order to encourage oviposition in a localized area within a breeding cage, the flies need to find the characteristics of an egg laying area or surface compelling over other areas within the breeding cage.

Upon arrival at a potentially suitable oviposition substrate, adult female BSF have been observed to drag the tip of their abdomen containing the ovipositor, along the surface of the substrate as a means for detecting a suitable oviposition site. Upon identification of a suitable site on a substrate, the adult female BSF extends her ovipositor outwardly and begins laying eggs at that site. Adult female BSF are known to seek out oviposition sites which provide natural protection to her when ovipositing and to the eggs and emergent neonate larvae. Adult female BSF are known to prefer recesses and/or corners within which to lay eggs. Characteristics such as inter alia the surface texture, shape and dimensions of surface features of an oviposition site play an important role in site selection and oviposition behaviour of adult female BSF. The size of the individual eggs deposited is small but due to the relatively large number of eggs oviposited by each female BSF, the eggs can cover a large surface area. The selection of an oviposition site having optimal characteristics is therefore crucial. The BSF female ovipositor has sensors that allow her to determine the most suitable site for her to lay her eggs. The sensors in the ovipositor are able to detect oviposition site characteristics including moisture, light, texture, shape, dimensions and odours. In a commercial BSF farming operation, in order to obtain an optimal yield of eggs, it is critically important to provide oviposition sites which will attract adult female BSF and encourage them to lay eggs on such sites.

Disadvantages associated with incorrect oviposition site location in commercial scale operations not only result in low harvest yields of eggs and neonates but may also result in a need to scrape eggs off from other sites resulting in high mortality or if this is not possible or feasible, emergence of neonate larvae inside adult fly cages necessitating additional management or removal of the neonates from the fly cages.

It is an object of the present invention to provide an oviposition tray for insect eggs having features which optimally attract and encourage adult female insects to lay of eggs on the oviposition tray.

SUMMARY OF THE INVENTION

According to the invention there is provided an oviposition tray for insect eggs, the oviposition tray comprising an oviposition tray body defining a plurality of elongate egg laying recesses in which eggs are laid, each recess having a length of between 10 mm and 25 mm, a width of between 1 mm and 10 mm and a depth of not less than 2 mm.

The width of each recess may optimally be approximately 2 mm.

Each recess may have a length of between 8 mm and 25 mm.

Each recess may have a length of between 10 mm and 20 mm.

Each recess may have a length of between 15 mm and 20 mm.

The length of each recess may optimally be approximately 17 mm.

The recesses may be spaced apart with a spacing between the recesses being between 1 mm and 6 mm. More specifically, the spacing between recesses may be approximately 2 mm.

Each recess may define a longitudinal axis along its length.

A number of the recesses may be arranged in spaced, parallel rows.

The oviposition tray body may have a colour defined by a colour space in accordance with the 1976 L* a* b* colour space (ISO standard ISO/CIE 11664-4:2019) of the International Commission on Illumination (CIE), wherein the colour space has a lightness value (L) of less than 90.

The lightness value (L) of the oviposition tray body may be less than 80.

The lightness value (L) of the oviposition tray body may be less than 70.

The colour space may have a green to red value (a*) of between −25 and +25 and a blue to yellow value (b*) of between −25 and +25.

The oviposition tray body may have a planar block configuration.

The oviposition tray body may have a front side and a rear side, with the recesses being defined in the front side of the oviposition tray body.

The front side of the oviposition tray body may define a flat face.

The oviposition tray body may define at least one aperture which extends between the rear side of the oviposition tray body and the front side of the oviposition tray body, the aperture allowing a flow of an airborne attractant substance therethrough in a direction from the rear side of the oviposition tray body to the front side thereof for attracting adult female insects to the oviposition tray in order to lay eggs in the recesses.

The oviposition tray body may include at least one spacer formation extending from the rear side thereof for abutment with the front side of another oviposition tray so as to space the oviposition tray from the another oviposition tray when the oviposition trays are arranged in a vertically stacked configuration.

The oviposition tray body may include a depression within which the spacer formation of another oviposition tray which is stacked on the oviposition tray, is received.

The oviposition tray body may include a number of the spacer formations located near peripheral edge regions of the oviposition tray body and a number of complementary depressions for receiving the spacer formations of other adjacent oviposition trays in a stacked configuration of the oviposition trays.

The oviposition tray body may include attachment means providing for attachment of the oviposition tray body to another oviposition tray or for conveying the oviposition tray.

The attachment means may comprise at least one passage which extends through the oviposition tray body and may include an elongate attachment rod which is received within the passage.

The oviposition tray body may be of moulded plastics material.

BRIEF DESCRIPTION OF THE DRAWINGS

Further features of the invention are described hereinafter by way of a non-limiting example of the invention, with reference to and as illustrated in the accompanying diagrammatic drawings. In the drawings.

DETAILED DESCRIPTION OF THE INVENTION

Figure 1:
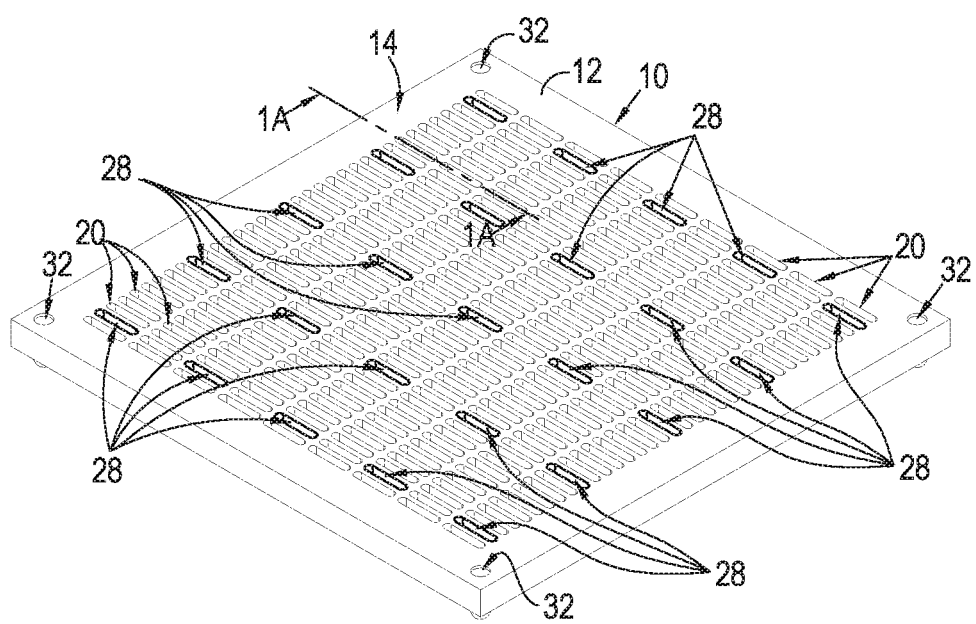
FIG. 1 shows a three-dimensional view, as seen from a front side thereof, of an oviposition tray in accordance with the invention.
Figure 1A:
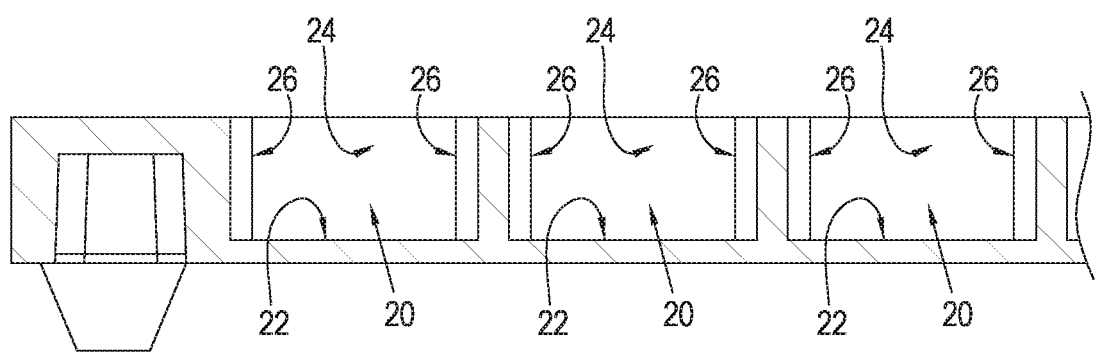
FIG. 1A shows a fragmentary sectional side view of the oviposition tray as sectioned along section line 1A-1A of FIG. 1.
Figure 2:
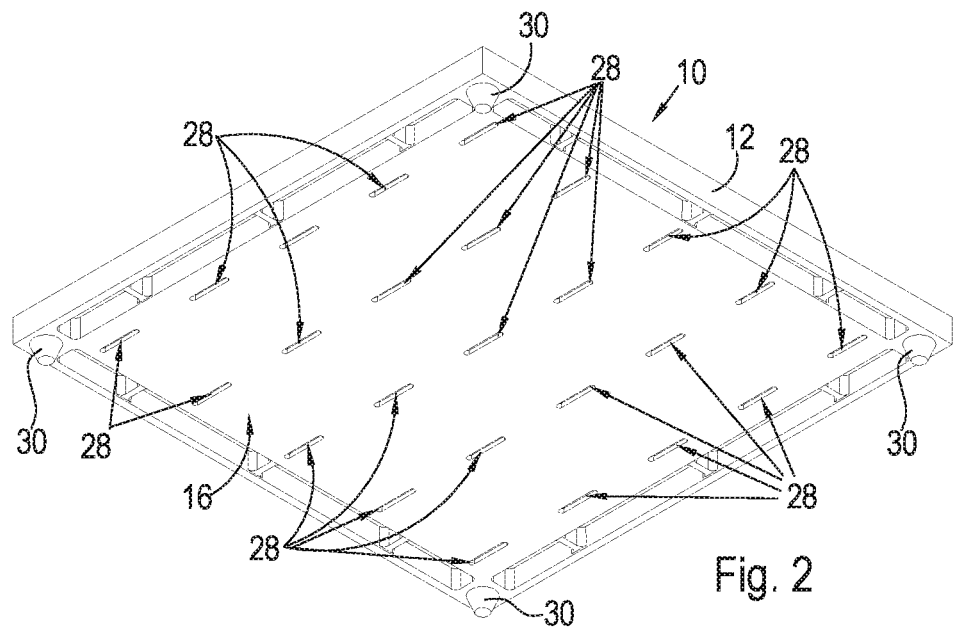
FIG. 2 shows a three-dimensional view, as seen from a rear side thereof, of the oviposition tray of FIG. 1.
Figure 3:
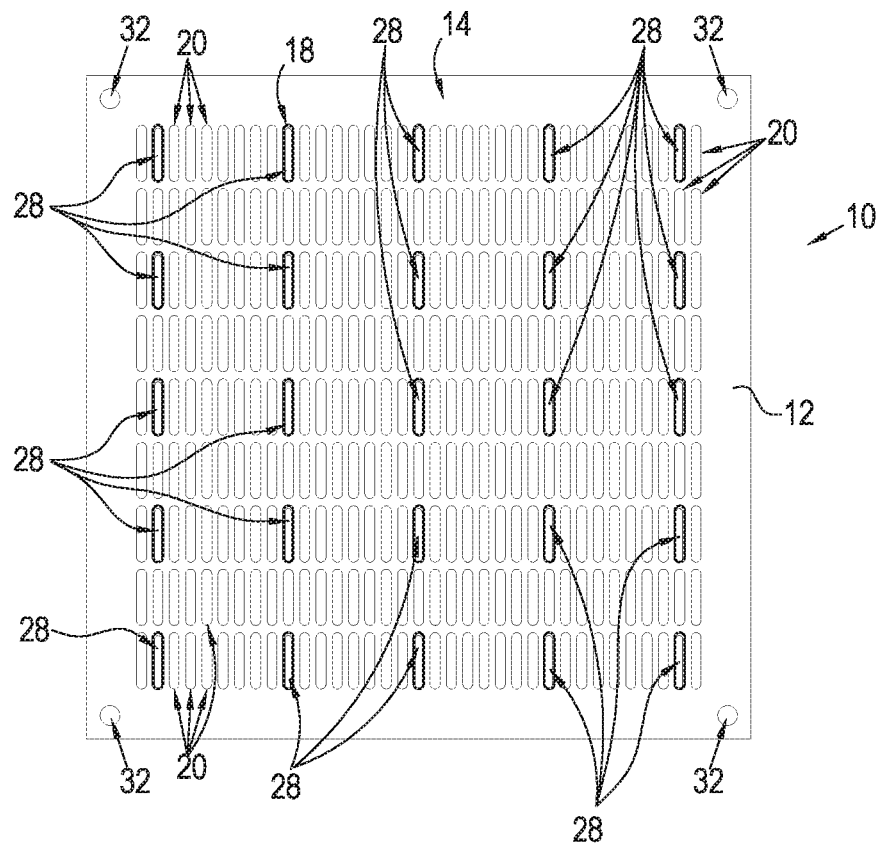
FIG. 3 shows a plan view of the oviposition tray of FIG. 1, as seen from the front side thereof.
Figure 4:
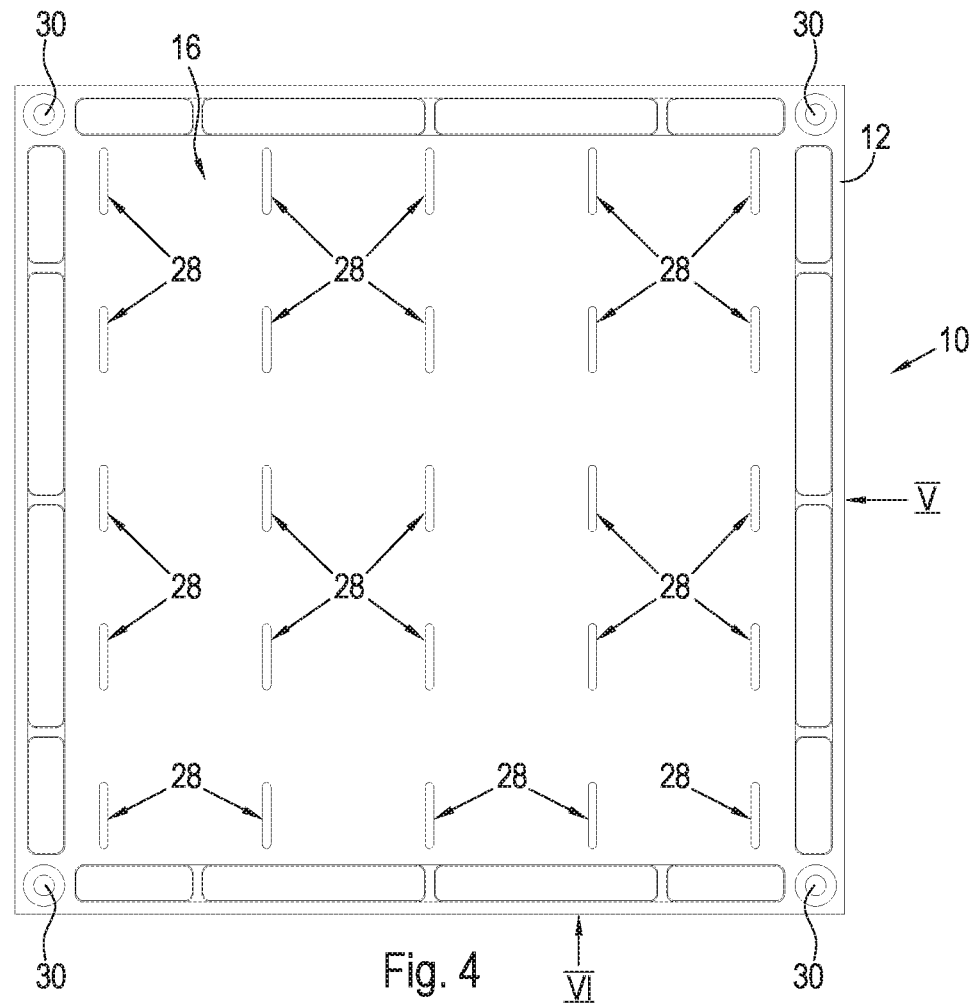
FIG. 4 shows a plan view of the oviposition tray of FIG. 1, as seen from the rear side thereof.
Figure 5:
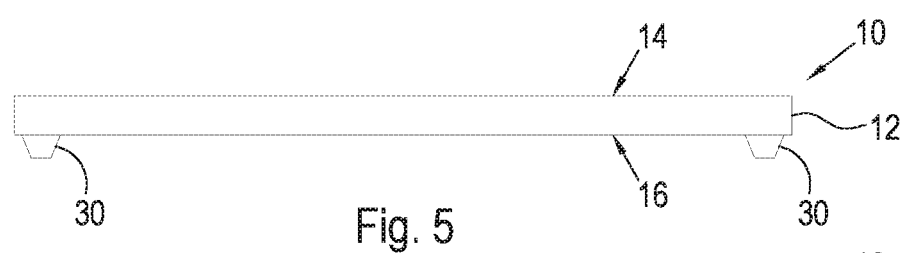
FIG. 5 shows an end view of the oviposition tray of FIG. 4, as seen from the direction of arrow V of FIG. 4.
Figure 6:
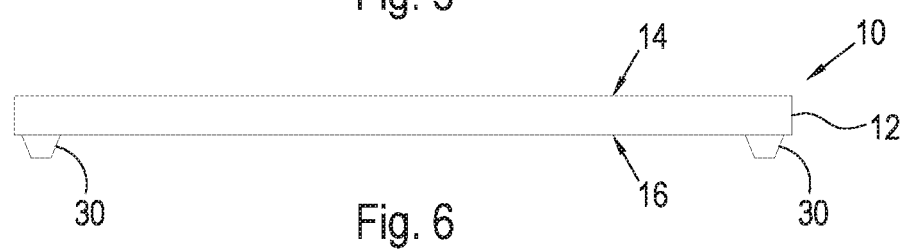
FIG. 6 shows an end view of the oviposition tray of FIG. 1, as seen from the direction of arrow VI of FIG. 4.

With reference to FIGS. 1 to 9 of the drawings, an oviposition tray for insect eggs, in accordance with the invention, is designated generally by the reference numeral 10. The oviposition tray 10 is configured for ovipositioning of insect eggs of a variety of useful insect species. More particularly, the oviposition tray 10 is adapted for ovipositioning of eggs of adult female BSF.

The oviposition tray comprises an oviposition tray body 12 of an injection moulded plastic material. The oviposition tray body has a generally planar square block configuration. The oviposition tray body has a front side 14 and a rear side 16. The front side 14 defines a flat face in which a plurality of elongate egg laying recesses 20 for receiving insect eggs laid by female BSF, are defined. The recesses 20 are in the form of elongate slots having longitudinal axes, arranged in spaced, parallel rows. Each recess is defined by a base wall 22 defining a base of the recess, a pair of straight spaced parallel side walls 24 defining sides of the recess and a pair of rounded end wall sections 26 defining opposite ends of the recess. Each recess defines a longitudinal axis along its length.

The oviposition tray body 12 defines a number of ventilation apertures 28 which extend between the rear side 16 and the front side 14 of the oviposition tray body 12. The ventilation apertures 28 have an elongate configuration which is similar to the configuration of the recesses and are located at predetermined positions within the rows of recesses 20. The ventilation apertures allow of an airborne attractant substance to flow through the oviposition tray body in a direction from the rear side of the oviposition tray body to the front side of the oviposition tray body for attracting adult female insects to the oviposition tray in order to lay eggs in the recesses 20 defined in the front side.

The oviposition tray body 12 includes four spacers in the form of feet 30, each spacer being located at a different corner of the oviposition tray body and extending rearwardly from the rear side of the oviposition tray body. The front side 14 of the oviposition tray body 12 defines a complementary depression 32 at each corner in which the foot 30 of an adjacent oviposition tray 10, is received in a stacked configuration of the oviposition trays.

Each recess 20 in the oviposition tray body optimally has a length of between 8 mm and 25 mm, preferably a length of between 10 mm and 20 mm, more preferably a length of between 15 mm and 20 mm and most optimally a length of approximately 17 mm. Experiments conducted by the Applicant on adult female BSF on a number of oviposition trays wherein the oviposition trays were identical with the only difference being a difference in the lengths of the recesses defined therein for oviposition, revealed a preference by adult BSF for recesses having lengths of between 8 mm and 25 mm, preferably a length of between 10 mm and 20 mm, more preferably a length of between 15 mm and 20 mm and optimally lengths of approximately 17 mm.

Each recess 20 optimally has a width of between 1 mm and 6 mm and most optimally a width of approximately 2 mm. In tests conducted by the Applicant on oviposition trays having recesses of a variety of different widths, an overwhelming preference for recesses having a width of approximately 2 mm, was observed. An optimal range of recess widths of between 1 mm and 6 mm was observed. Observations of oviposition behaviour of adult female BSF, suggest that recess widths of less than 1 mm make it difficult for adult female BSF to oviposit accurately with the recesses while recesses having widths larger than 6 mm provide limited environmental protection to the eggs and emergent neonates and are therefore not preferred. It was observed in this regard that adult female BSF would select an alternative oviposition site when the widths of recesses are below or above the preferred range.

Each recess 20 optimally has a depth of not less than 2 mm. A depth shallower than 2 mm was found in tests conducted by the Applicant, to not be preferred by adult female BSF. It is believed that the reason for this is that a depth of less than 2 mm offers too little protection to eggs and emergent neonates.

It has been observed in experiments conducted on oviposition trays, that the density of oviposition recesses in oviposition trays plays an important role in attracting and encouraging adult female BSF to lay eggs in the recesses. A spacing of approximately 2 mm between recesses was observed by the Applicant to be optimal.

It has furthermore been observed by the Applicant that recesses having an elongate shape are preferred by adult female BSF as oviposition sites.

In addition, it has been observed in experiments conducted by the Applicant that a repeating pattern of elongate recesses wherein the recesses are arranged in rows in which the spacing between recesses is as described hereinabove, appears to attract adult female BSF to the oviposition tray.

Extensive research has been carried out by the Applicant on the impact of ambient light and colour on the fly colony. It has been shown that the colour of light has a direct bearing on the mating and laying activities of adult female BSF. It was reasonable to expect that the light conditions reflect weather conditions that would give rise to optimal mating activity in the wild and this has been found to be true in experiments conducted by the Applicant.

Furthermore, the Applicant believes that it would be fair to assume that if a female fly is motivated to lay her eggs in or near to an available food source (for the emergent larvae) that there would be a typical colour that best represents this type of food source.

Tests were conducted by the Applicant across a selection of oviposition trays of different colours. A clear preference by adult BSF for oviposition trays having a relatively dark shade of colour, was observed. Bright colours were avoided by adult female BSF, possibly due to the fact that in the wild traditionally brighter colours are an indication of living plants and animals not suitable as food for emergent larvae. Furthermore, it is likely that a dark colour represents an oviposition site in nature which is in a darker location shaded from ambient light such as a recess or protected environment which encourages oviposition. It was found in experiments conducted by the Applicant with oviposition trays of different colours, that darker shades of grey are particularly attractive to adult female BSF as oviposition sites. More specifically, it was found that an oviposition tray body of a colour defined by a colour space having a lightness value (L) of less than 90, a green to red value (a) of between −25 and +25 and a blue to yellow value (b) of between −25 and +25 in accordance with the 1976 L* a* b* colour space (ISO standard ISO/CIE 11664-4:2019) of the International Commission on Illumination (CIE), provided a higher yield of eggs. The yield of eggs oviposited on oviposition trays increased further with measured lightness values (L) of less than 80 and yet further with measured lightness values (L) of less than 70.

Figure 7:
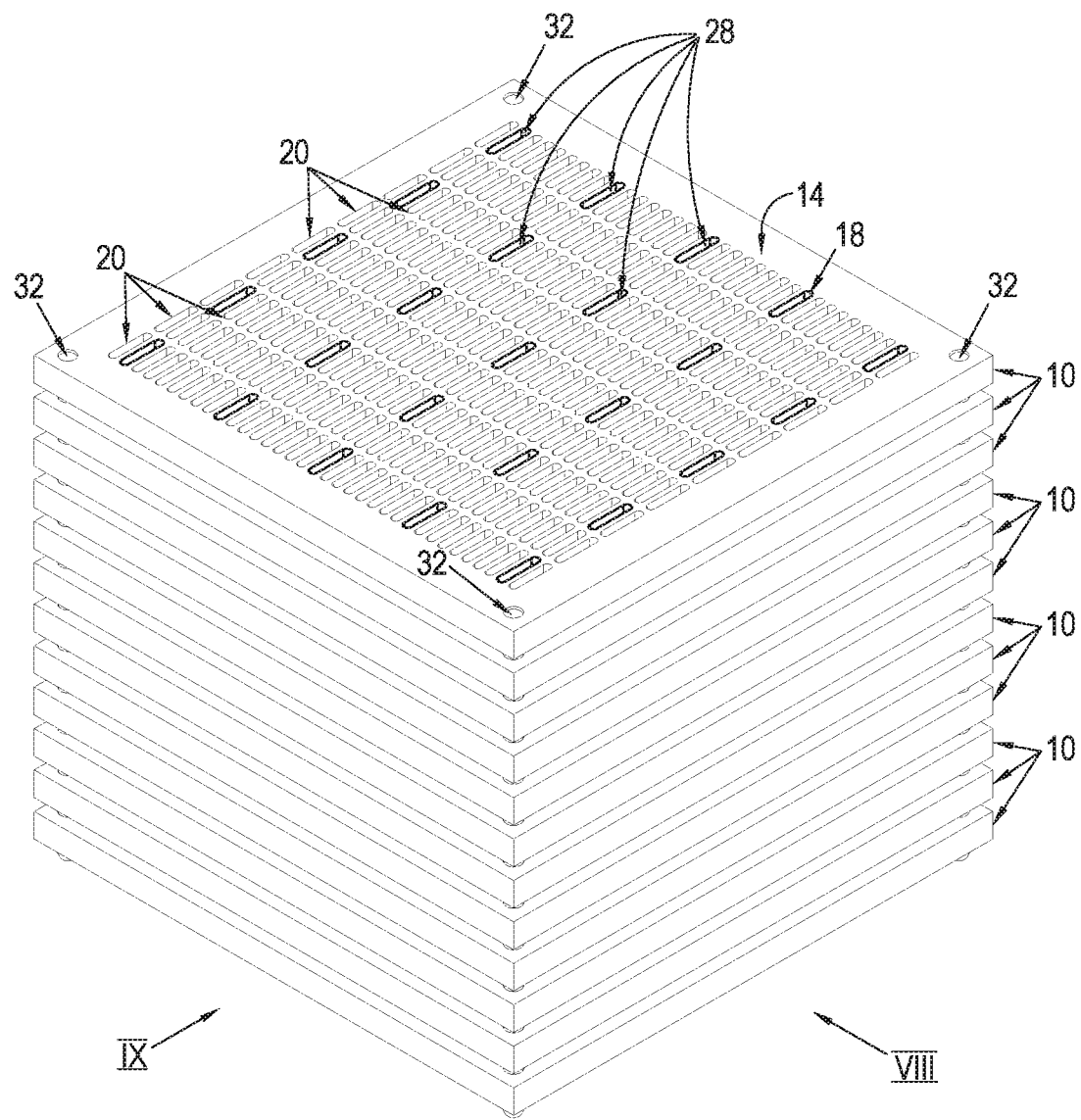
FIG. 7 shows a three-dimensional view of a number of the oviposition trays of FIG. 1 stacked on top of one another.
Figure 8:
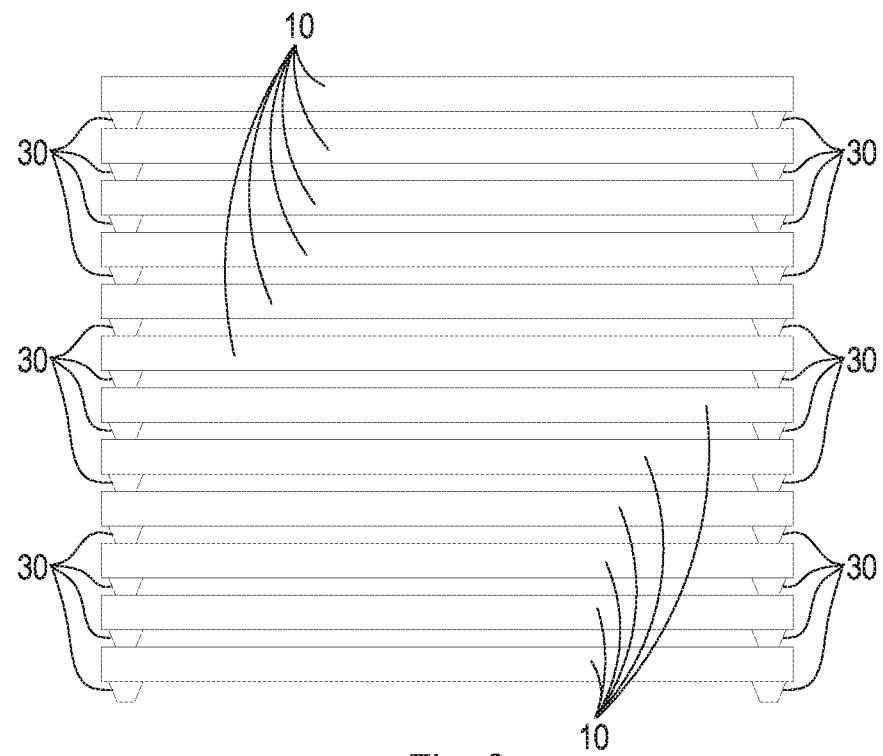
FIG. 8 shows a side view of the stack of oviposition trays of FIG. 7 as seen from the direction of arrow VIII of FIG. 7.
Figure 9:
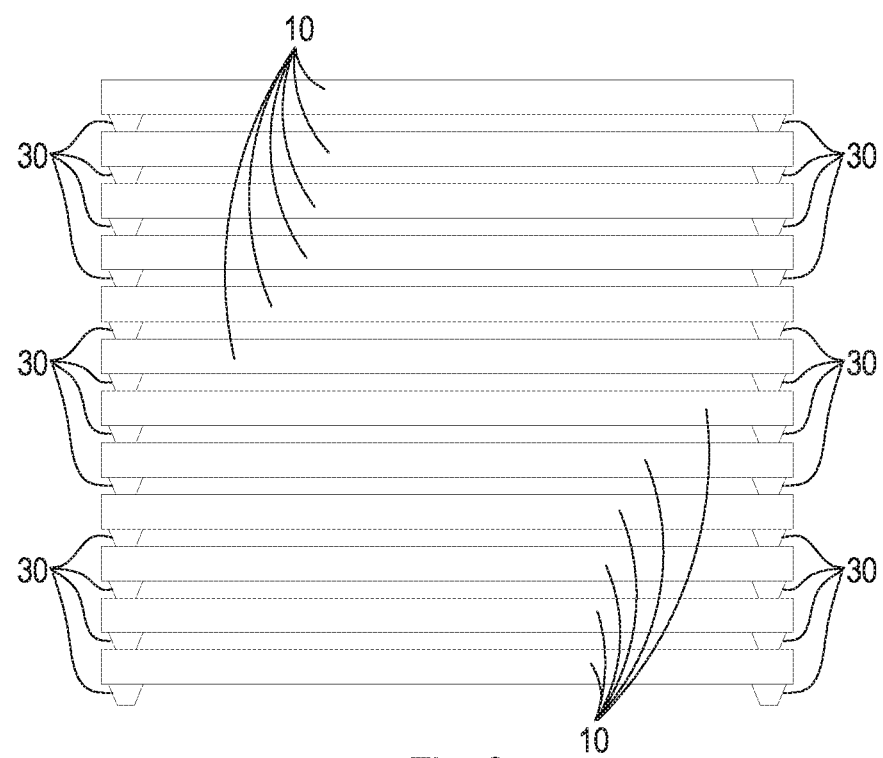
FIG. 9 shows a side view of the stack of oviposition trays of FIG. 7 as seen from the direction of arrow IX of FIG. 7.
Figure 10:
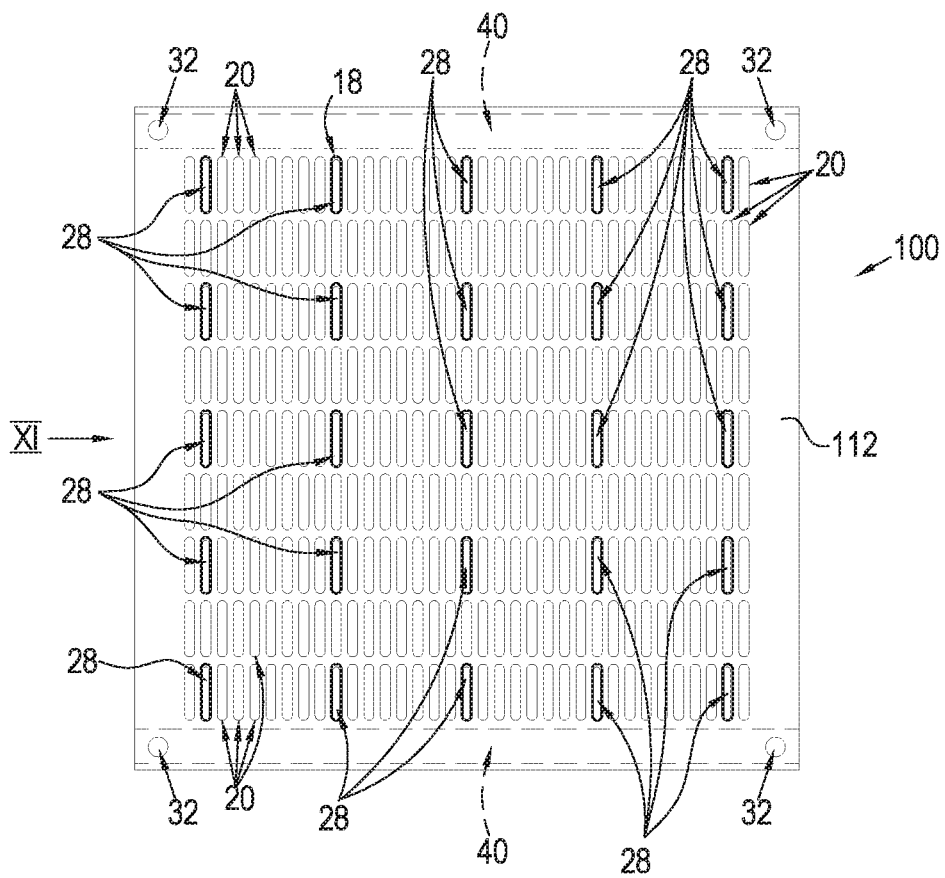
FIG. 10 shows a plan view of a front side of another embodiment of an oviposition tray in accordance with the invention.
Figure 11:
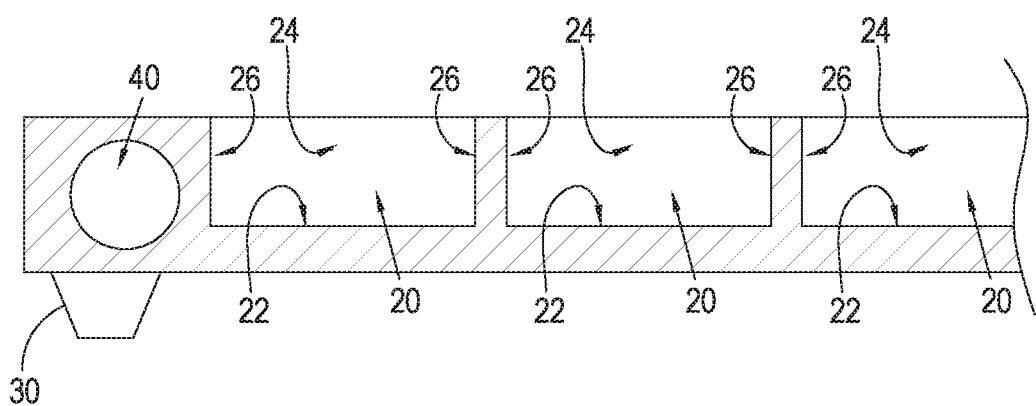
FIG. 11 shows an end view of the oviposition tray of FIG. 10 as seen from the direction of arrow XII.
Figure 12:
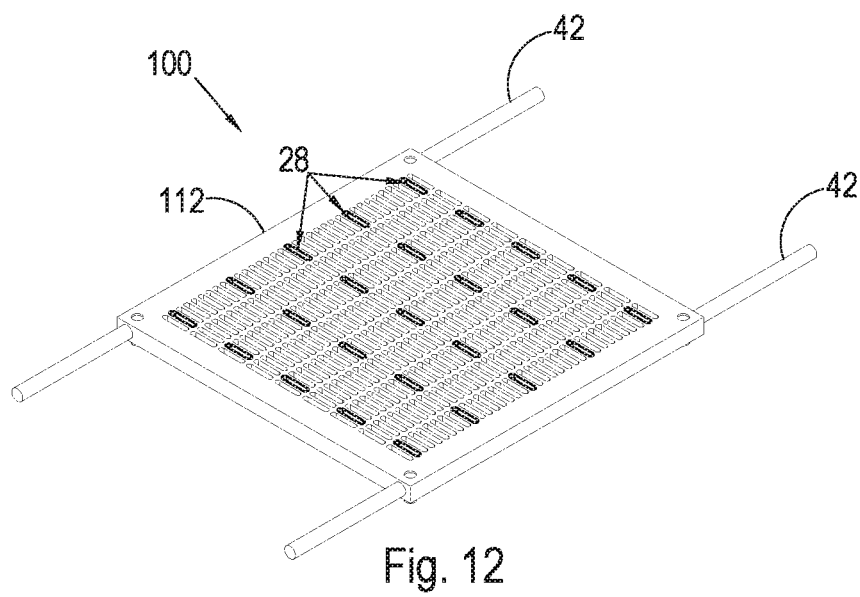
FIG. 12 shows a three-dimensional view of the oviposition tray of FIG. 10 including a pair of attachment rods for attaching the oviposition tray to other oviposition trays and/or for conveying the oviposition tray.

In FIGS. 7 to 9 of the drawings, a number of the oviposition trays 10 are shown in a stacked configuration wherein the oviposition trays are stacked on top of one another. In the stacked configuration, adjacent oviposition trays are securely located relative to one another by means of the feet 30 and complementary recesses 32 in which ends of the feet 30 are snugly received. The depressions 32 are relatively shallow such that the feet 30 of adjacent oviposition trays are long enough to adequately space the adjacent oviposition trays from one another. The stacked configuration of the oviposition trays provides a compact space-saving arrangement which aids in the collection and transport of the oviposition trays to a location where eggs oviposited on the oviposition trays are stowed until neonate larvae emerge from the eggs. The stacked configuration of the oviposition trays provides an optimally dark environment in the spaces between the oviposition trays, which is conducive to hatching of the eggs and which also enhances survivability of emergent neonate larvae.

With reference to FIGS. 10 to 13 of the drawings, another embodiment of an oviposition tray in accordance with the invention, is designated generally by the reference numeral 100. The oviposition tray 100 is similar to the oviposition tray 10 with the only difference being that the oviposition tray 100 is configured to be attached and/or conveyed. In FIGS. 10 to 13 of the drawings, those features of the oviposition tray 100 which are the same as and/or similar to those features of the oviposition tray 10, are designated by the same and/or similar reference numerals.

The oviposition tray 100 includes a pair of elongate passages 40 in which attachment rods 42 are received for attaching the oviposition trays to one another and/or conveying the oviposition trays.

Figure 13:
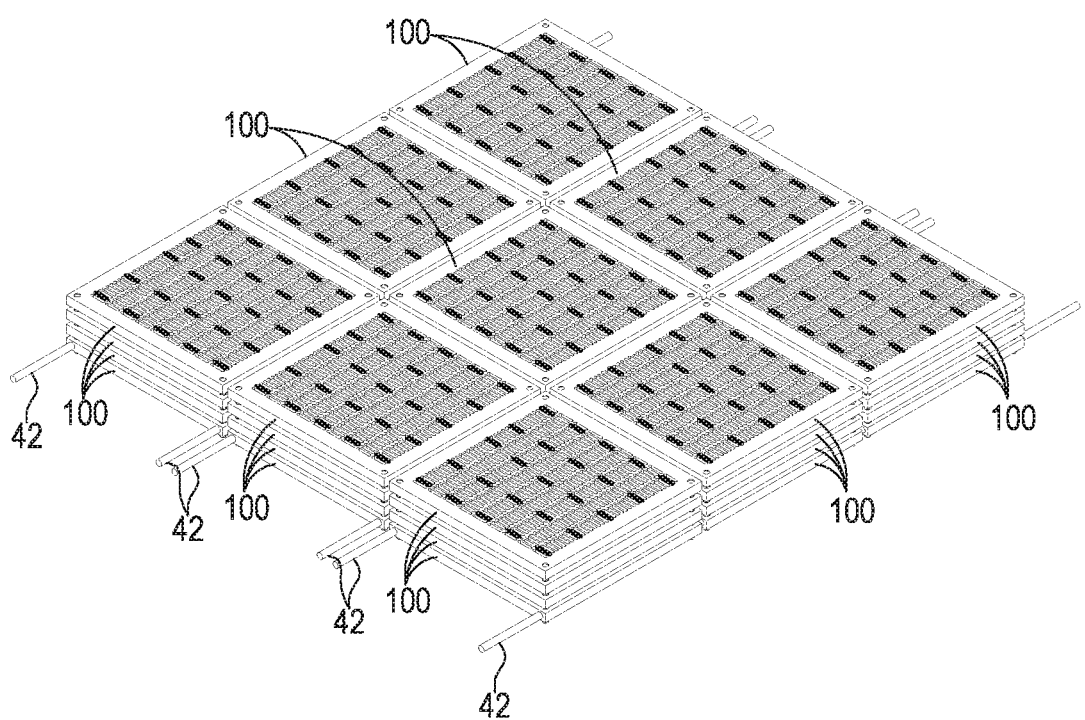
FIG. 13 shows a number of the oviposition trays of FIG. 10 in a stacked configuration.

As for the oviposition tray 10, the oviposition tray 100 can be stacked in a stacked configuration shown in FIG. 13 in order to provide a compact space-saving arrangement and an environment which is conducive to hatching of insect eggs deposited on the oviposition trays and survivability of emergent neonate larvae.

The invention claimed is:

1. An oviposition tray for insect eggs, the oviposition tray comprising:
   an oviposition tray body defining a plurality of elongate egg laying recesses in which eggs are laid, each recess having a length of at least 8 mm, a width of between 1 mm and 6 mm, and a depth of not less than 2 mm,
   wherein the oviposition tray body has a front face and a rear face, with the recesses being defined in the front face of the oviposition tray body, and
   wherein the oviposition tray body defines a plurality of apertures, each aperture configured to extend between the rear face of the oviposition tray body and the front face of the oviposition tray body, the plurality of apertures being intermixed among the plurality of elongate egg laying recesses,
   wherein the plurality of apertures are configured to allow a flow of an airborne attractant substance therethrough in a direction from the rear face of the oviposition tray body to the front face thereof for attracting adult female insects to the oviposition tray in order to lay eggs in the recesses.

2. The oviposition tray as claimed in claim 1, wherein the width of each recess is approximately 2 mm.

3. The oviposition tray as claimed in claim 1, wherein each recess has a length of between 8 mm and 25 mm.

4. The oviposition tray as claimed in claim 1, wherein each recess has a length of between 10 mm and 20 mm.

5. The oviposition tray as claimed in claim 1, wherein each recess has a length of between 15 mm and 20 mm.

6. The oviposition tray as claimed in claim 1, wherein the length of each recess is approximately 17 mm.

7. The oviposition tray as claimed in claim 1, wherein the recesses are spaced apart with a spacing between the recesses being between 1 mm and 6 mm.

8. The oviposition tray as claimed in claim 7, wherein the spacing between recesses is approximately 2 mm.

9. The oviposition tray as claimed in claim 1, wherein each recess defines a longitudinal axis along a length of the respective recess.

10. The oviposition tray as claimed in claim 1, wherein a number of the recesses are arranged in spaced, parallel rows.

11. The oviposition tray as claimed in claim 10, wherein the oviposition tray body has a colour defined by a colour space in accordance with the 1976 L* a* b* colour space (ISO standard ISO/CIE 11664-4:2019) of the International Commission on Illumination (CIE), wherein the colour space has a lightness value (L) of less than 90.

12. The oviposition tray as claimed in claim 11, wherein the lightness value (L) of the oviposition tray body is less than 80.

13. The oviposition tray as claimed in claim 11, wherein the lightness value (L) of the oviposition tray body is less than 70.

14. The oviposition tray as claimed in claim 11, wherein the colour space has a green to red value (a*) of between −25 and +25 and a blue to yellow value (b*) of between −25 and +25.

15. The oviposition tray as claimed in claim 1, wherein the oviposition tray body has a planar block configuration.

16. The oviposition tray as claimed in claim 1, wherein the front face of the oviposition tray body defines a flat face.

17. The oviposition tray as claimed in claim 1, wherein the oviposition tray body includes at least one spacer formation extending from the rear face thereof for abutment with the front face of another oviposition tray so as to space the oviposition tray from the another oviposition tray when the oviposition trays are arranged in a vertically stacked configuration.

18. The oviposition tray as claimed in claim 17, wherein the oviposition tray body includes a depression within which the spacer formation of another oviposition tray which is stacked on the oviposition tray, is received.

19. The oviposition tray as claimed in claim 18, wherein the oviposition tray body includes a number of the spacer formations located near peripheral edge regions of the oviposition tray body and a number complementary depressions for receiving the spacer formations of other adjacent oviposition trays in a stacked configuration of the oviposition trays.

20. The oviposition tray as claimed in claim 1, wherein the oviposition tray body includes attachment means providing for attachment of the oviposition tray body to another oviposition tray or for conveying the oviposition tray.

21. The oviposition tray as claimed in claim 20, wherein the attachment means comprises at least one passage which extends through the oviposition tray body and includes an elongate attachment rod which is received within the passage.

22. The oviposition tray as claimed in claim 1, wherein the oviposition tray body is of moulded plastics material.

* * * * *